United States Patent

Scavino

[11] 4,122,111
[45] Oct. 24, 1978

[54] CARBAMOYLTHIOBENZAMIDES AND COMPOSITIONS COMPRISING SAME

[75] Inventor: Carlo Scavino, Milan, Italy

[73] Assignee: ISF Spa, Milan, Italy

[21] Appl. No.: 793,543

[22] Filed: May 4, 1977

[30] Foreign Application Priority Data

May 7, 1976 [IT] Italy ................. 23066 A/76

[51] Int. Cl.² .............. C07C 153/09; A61K 31/27
[52] U.S. Cl. ........................ 424/300; 260/455 A;
260/544 P; 260/558 S
[58] Field of Search ................... 260/455 A

[56] References Cited

U.S. PATENT DOCUMENTS 3,865,867   2/1975   Olin et al. ............. 260/455 A
3,884,951   5/1975   Oswald ................. 260/455 A Primary Examiner—Lewis Gotts
Assistant Examiner—Robert C. Whittenbaugh
Attorney, Agent, or Firm—Depaoli & O'Brien

[57] ABSTRACT

Biologically active derivatives of benzamide and methods for preparation thereof are disclosed. These derivatives specifically have anti-fungal activity and are characterized by the following general formula:

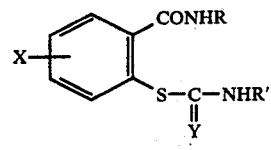

wherein R is H or a saturated or unsaturated alkyl radical of 1–6 carbons; R' is a nitro group, a halogen, a saturated or unsaturated alkyl radical of 1–6 carbons, a cycloalkyl radical of 5 or 6 carbons, or a phenyl, benzyl, or naphthyl radical that is mono- or bis-substituted with a lower alkyl or alkoxy radical; X is H, a lower alkyl radical, or a halogen; and Y is O or S.

10 Claims, No Drawings

CARBAMOYLTHIOBENZAMIDES AND COMPOSITIONS COMPRISING SAME

The present invention is concerned with biologically-active derivatives of benzamide with the preparation thereof. More particularly, the aim of the present invention consists in the new derivatives with antifungine activity of general formula:

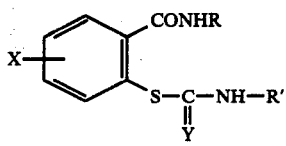

wherein R is hydrogen, alkyl radical containing from 1 to 6 carbon atoms, R' is an alkyl radical containing from 1 to 6 carbon atoms, a cycloalkyl radical containing 5 or 6 carbon atoms, an aryl radical, X is a hydrogen atom, a lower alkyl radical, a halogen atom, Y is oxygen and sulphur.

The term alkyl radical containing from 1 to 6 carbon atoms comprises saturated, unsaturated alkyl radicals having linear or branched chain: more particularly, it comprises among others methyl, ethyl, propyl, butyl, pentyl, hexyl, isopropyl, isobutyl, t.butyl, isopentyl, t.pentyl, isohexyl, allyl, vinyl, isopropenyl, ethinyl, propargyl.

The term cycloalkyl radical containing 5 to 6 carbon atoms comprises among the others cyclopentyl and cyclohexyl radicals.

The term aryl radical comprises among the others phenyl, and naphthyl radicals optionally substituted with one or more lower alkyl, lower alkoxy, nitro and halogen groups. The term lower alkyl and lower alkoxy radical mean alkyl and alkoxy radicals containing from 1 to 3 carbon atoms such as methyl, ethyl, propyl, methoxy, ethoxy and propoxy.

According to the process of the present invention, the compounds of formula I are prepared starting from dithiodiphenyldicaroxilic acids V which are at first a) chlorurated to the corresponding dichlorides IV, b) treated with a suitable amine to give diamides III, then c) reduced by means of zinc and a strong mineral acid to thioamide II and finally d) added to a suitable isocyanate or isothiocyanate. Schematically the process can be indicated as follows:

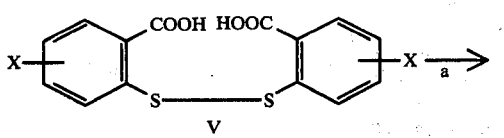

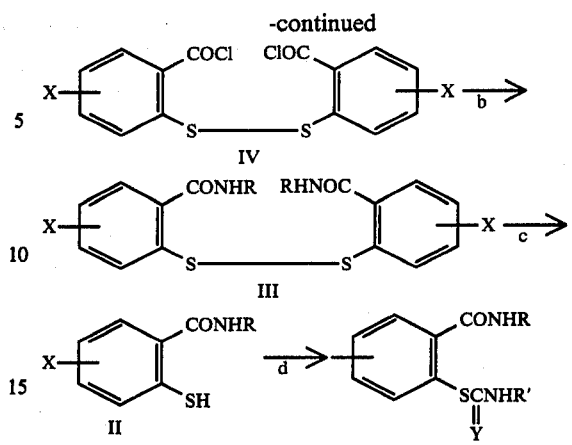

wherein R', R, Y and X have the above meaning. More specifically, the reaction a) is carried out in anhydrous conditions in an aprotic solvent, for example chlorurated hydrocarbons such as methylene chloride, chloroform, 1,2-dichloroethane or benzene and toluene at the boiling temperature of the solvent. Thionyl chloride, phosphorus oxychloride or preferably phosphorus pentachloride can be used as chlorurating agents. The reaction b) is carried out in aqueous ambient in a suitable aprotic polar solvent such as for example dioxane, tetrahydrofurane or dimethoxyethane in the presence of excess amine $RNH_2$ wherein R has the above meaning, or alternatively with the stoichiometric quantity of an amine $RNH_2$, wherein R has the above meaning, and a tertiary base. Such a reaction, preferably carried out in the cold in the first step, is completed at a temperature of 25° C. to 60° C. The reduction reaction c) is carried out in aqueous alcoholic ambient by means of a suitable reducing agent such as zinc in the presence of a strong mineral acid; among the preferred acids hydrochloric acid and sulphuric acid are more frequently used.

Finally, in the d) reaction the thiol obtained in the previous step is reacted in the warm in a suitable anhydrous aprotic solvent, with the suitable isocyanate or isothiocyanate R'-NCY where R' and Y have the above meaning preferably in the presence of an alcoholate of an alkaline metal such as for example potassium terbutylate. The compounds of formula I so obtained are isolated in a manner known per se.

The compounds of the invention possess an interesting antifungine and anti-Candida activity. They were tested in vitro according to the minimum inhibiting concentration (MIC) technique both in liquid and agar broth culture, compared to 8-hydroxyquinoline, a commercial product known for its antifungine and anti-Candida activity. Compared to such a standard the products of the invention are all decidedly more active both as antifungine and anti-Candida agents. The results obtained, expressed in mcg/ml are reported in the following table.

TABLE

| | N-Ethyl-o.(N-Ethylcarbamoylthio)benzamide Example 1 | N-Ethyl-o.(N-methylcarbamoylthio)benzamide Example 4 | N-Ethyl-o.(N-methylthiocarbamoylthio)benzamide Example 23 | N-Methyl-2-(N-methylcarbamoylthio)-5-chloro benzamide Example 21 | N-Ethyl-o.(N-allylcarbamoylthio)benzamide Example 25 | 8-hydroxy quinoline |
|---|---|---|---|---|---|---|
| Trichophyton mentagrophytes | 0.39 | 0.78 | 0.78 | 0.78 | 0.39 | 1.56 |
| Trichophyton tonsurans | 0.39 | 0.19 | 0.19 | 0.78 | 0.19 | 1.56 |
| Epidermophyton floccosum | 0.78 | 0.19 | 0.19 | 0.19 | 0.78 | 1.56 |
| Microsporum canis | 1.56 | 3.12 | 0.78 | 0.19 | 0.19 | 1.56 |
| Candida albicans 1 | 3.12 | 3.12 | 1.56 | 1.56 | 1.56 | 6.25 |

TABLE-continued

|  | N-Ethyl-o.(N-Ethylcarbamoylthio)benzamide Example 1 | N-Ethyl-o.(N-methylcarbamoylthio)benzamide Example 4 | N-Ethyl-o.(N-methylthiocarbamoylthio)benzamide Example 23 | N-Methyl-2-(N-methylcarbamoylthio)-5-chlorobenzamide Example 21 | N-Ethyl-o.(N-allylcarbamoylthio)benzamide Example 25 | 8-hydroxy quinoline |
|---|---|---|---|---|---|---|
| Candida albicans 2 | 3.12 | 3.12 | 1.56 | 1.56 | 1.56 | 12.5 |

The following Examples are given for the purpose of illustrating the present invention without limiting it.

EXAMPLE 1

N-Ethyl-o.(N-ethylcarbamoylthio)benzamide

Grams 92 of 2,2'-dicarboxydiphenyldisulphide are added to 450 ml of anhydrous benzene with 167 g of phosphorus pentachloride: the mixture is boiled until solution and heating is prolonged for a further 30 minutes.

The resulting mixture is filtered on a little charcoal and 450 ml of ligroine are added in the warm. A precipitate is obtained by cooling, which is filtered and washed with petrol ether.

The raw product is recrystallized from benzene/ligroine. Grams 73 of dichloride of 2,2'-dicarboxydiphenyldisulphide are obtained, melting at 152°–154° C. The product obtained, suspended in 350 ml dioxane, is added in the cold to 140 ml of 33% ethylamine aqueous solution. The resulting mixture is left to stand for an hour, heated to 50° C. on a waterbath for a further hour and finally poured into ice and water. The product which separates is filtered off and washed with water. The resulting product is crystallized dissolving it in 1000 ml ethyl alcohol, decolorating on charcoal and adding water in the hot until incipient precipitation. Grams 60 N,N'-bis-ethylamide of 2,2'-dicarboxydiphenyldisulphide melting at 200°–202° C. are obtained. The product obtained, in 250 ml ethyl alcohol and 50 ml of water is reduced with 60 g of zinc chips and 200 ml of concentrated hydrochloric acid. The reaction mixture is kept boiling for 30 minutes; the excess zinc is then filtered off; the filtrate is concentrated under vacuo until small volume and diluted with a little water and ice; the product obtained is washed with little water until neutrality and recrystallized from carbon tetrachloride decolorating with adsorbing charcoal. Grams 51 N-ethylthiosalicylamide are obtained which in 260 ml anhydrous benzene at 50°–60° C. are added of 25.8 ml potassium terbutilate and of 23.9 ml ethylisocyanate dissolved in 130 ml benzene.

The product is left to stand for one night and then concentrated until incipient crystallization; 390 ml petrol are then added and the mixture cooled. The product which separates is filtered off and recrystallized from 400 ml ethyl acetate.

Grams 46 N-ethyl-o.(N-ethylcarbamoylthio)benzamide melting at 120°–124° C. are obtained.

EXAMPLES 2-25

Operating as described in Example I, the compounds indicated in the following table are obtained. The melting points given in the table generally show decomposition.

| EX | R | R' | X | Y | M.P. in °C |
|---|---|---|---|---|---|
| 2 | CH₃ | CH₃ | H | O | 224-5 |
| 3 | CH₃ | C₂H₅ | H | O | 162-3 |
| 4 | C₂H₅ | CH₃ | H | O | 187-9 |
| 5 | C₂H₅ | nC₃H₇ | H | O | 134-6 |
| 6 | C₂H₅ | C₃H₇iso | H | O | 153-5 |
| 7 | C₂H₅ | nC₄H₉ | H | O | 120-2 |
| 8 | C₂H₅ | tC₄H₉ | H | O | 157-9 |
| 9 | C₂H₅ | C₆H₁₁ | H | O | 165-7 |
| 10 | C₂H₅ | C₆H₅ | H | O | 172-4 |
| 11 | C₂H₅ | 3,CH₃C₆H₄ | H | O | 159-61 |
| 12 | C₂H₅ | 4,CH₃C₆H₄ | H | O | 181-3 |
| 13 | C₂H₅ | 4,CH₃OC₆H₄ | H | O | 160-2 |
| 14 | C₂H₅ | 3,ClC₆H₄ | H | O | 152-4 |
| 15 | C₂H₅ | 4ClC₆H₄ | H | O | 192-4 |
| 16 | C₂H₅ | 4NO₂C₆H₄ | H | O | 200-2 |
| 17 | C₂H₅ | 3,4Cl₂C₆H₃ | H | O | 179-81 |
| 18 | C₂H₅ | α-naphthyl | H | O | 183-5 |
| 19 | nC₄H₉ | CH₃ | H | O | 134-6 |
| 20 | nC₆H₁₃ | CH₃ | H | O | 151-3 |
| 21 | CH₃ | CH₃ | 5Cl | O | 164-6 |
| 22 | CH₃ | C₂H₅ | 5Cl | O | 169-71 |
| 23 | C₂H₅ | CH₃ | H | S | 113-5 |
| 24 | C₂H₅ | C₂H₅ | 5CH₃ | O | 158-60 |
| 25 | C₂H₅ | CH₂CH=CH₂ | H | O | 135-8 |

I claim:

1. Process for the preparation of compounds having the general formula:

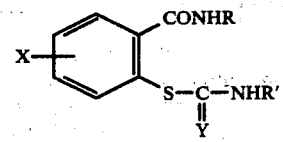

wherein:
R is a hydrogen or a saturated or unsaturated alkyl radical containing 1 through 6 carbon atoms;
R' is:
  a saturated or unsaturated alkyl radical containing 1 through 6 carbon atoms,
  a cycloalkyl radical containing 5 or 6 carbon atoms,
  a phenyl, benzyl, or naphthyl radical that is mono- or bis-substituted with an alkyl or alkoxy radical containing 1 through 3 carbon atoms,
  a nitro group, or
  a halogen;
X is:
  hydrogen,
  an alkyl radical containing 1 through 3 carbon atoms, or
  a halogen; and
Y is an oxygen or sulfur atom, characterized by heating a dithiodiphenylcarboxylic acid, having the general formula:

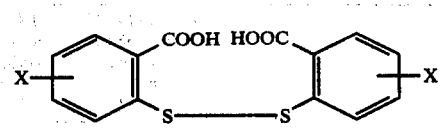

wherein X is said X, in anhydrous conditions and in an aprotic solvent with a suitable chlorinating agent to form a dithiodiphenyl acid chloride, reacting said dithiodiphenyl acid chloride in an aqueous aprotic polar solvent with an amine RNH$_2$, wherein R is said R, to form a dithiodiphenylamide, reducing said dithiodiphenylamide in aqueous alcoholic ambient to form a thioamide, and reacting said thioamide in a warm anhydrous aprotic solvent with the compound R'-NCY, wherein R' is said R' and Y is said Y, to form said compounds having the general formula:

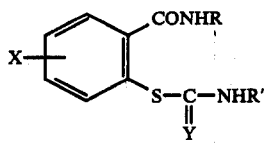

wherein R, R', X, and Y are said R, R', X, and Y.

2. Compounds having the general formula:

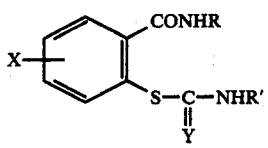

wherein:
R is hydrogen or a saturated or unsaturated alkyl radical containing 1 through 6 carbon atoms;
R' is:
   a saturated or unsaturated alkyl radical containing 1 through 6 carbon atoms,
   a cycloalkyl radical containing 5 or 6 carbon atoms,
   a phenyl, benzyl, or naphthyl radical that is mono- or bis-substituted with an alkyl or alkoxy radical containing 1 through 3 carbon atoms,
   a nitro group, or
   a halogen;
X is:
   hydrogen,
   an alkyl radical containing 1 through 3 carbon atoms, or
   a halogen; and
Y is oxygen or sulfur.

3. A pharmaceutical composition comprising a suitable diluent and at least one compound having the general formula of claim 2.

4. N-Ethyl-2-(N-ethylcarbamoylthio)-5-methylbenzamide.

5. N-Methyl-2-(N-methylcarbamoylthio)-5-chlorobenzamide.

6. N-Ethyl-o-(N-ethylcarbamoylthio)benzamide.

7. N-Allyl-o-(N-ethylcarbamoylthio)benzamide.

8. N-Ethyl-o-(N-methylcarbamoylthio)benzamide.

9. N-Ethyl-o-(N-methylthiocarbamoylthio)benzamide.

10. A pharmaceutical composition comprising a suitable diluent and at least one compound selected from the group consisting of:
   N-Ethyl-o-(N-ethylcarbamoylthio)benzamide,
   N-Ethyl-2-(N-ethylcarbamoylthio)-5-methylbenzamide,
   N-Allyl-o-(N-ethylcarbamoylthio)benzamide,
   N-Ethyl-o-(N-methylcarbamoylthio)benzamide,
   N-Ethyl-o-(N-methylthiocarbamoylthio)benzamide, and
   N-Methyl-2-(N-methylcarbamoylthio)-5-chlorobenzamide.

* * * * *

UNITED STATES PATENT OFFICE
CERTIFICATE OF CORRECTION

Patent No. 4,122,111          Dated October 24, 1978

Inventor(s) Carlo Scavino

It is certified that error appears in the above-identified patent and that said Letters Patent are hereby corrected as shown below:

In the ABSTRACT, that portion of the formula definition reading

R' is a nitro group, a halogen, a saturated or unsaturated alkyl radical of 1-6 carbons, a cycloalkyl radical of 5 or 6 carbons, or a phenyl, benzyl, or naphthyl radical that is mono- or bis-substituted with a lower alkyl or alkoxy radical;

should read

R' is a saturated or unsaturated alkyl radical of 1-6 carbons, a cycloalkyl radical of 5 or 6 carbons, or a phenyl, benzyl, or naphthyl radical that is mono- or bis-substituted with a lower alkyl or alkoxy radical, with a nitro group, or with a halogen;

In Column 4, lines 47-51, that portion of the formula reading
    a phenyl, benzyl, or naphthyl radical that is mono- or bis-substituted with an alkyl or alkoxy radical containing 1 through 3 carbon atoms,
      a nitro group, or
      a halogen;
should read
    a phenyl, benzyl, or naphthyl radical that is mono- or bis-substituted with an alkyl or alkoxy radical containing 1 through 3 carbon atoms, with a nitro group, or with a halogen;

In Column 5, lines 32-36 and Column 6, lines 1-5, that portion of the formula reading
    a phenyl, benzyl, or naphthyl radical that is mono- or bis-substituted with an alkyl or alkoxy radical containing 1 through 3 carbon atoms,
      a nitro group, or
      a halogen;

UNITED STATES PATENT OFFICE
CERTIFICATE OF CORRECTION

Patent No. 4,122,111  Dated October 24, 1978

Inventor(s) Carlo Scavino

It is certified that error appears in the above-identified patent and that said Letters Patent are hereby corrected as shown below:

should read
    a phenyl, benzyl, or naphthyl radical that is mono- or bis-substituted with an alkyl or alkoxy radical containing 1 through 3 carbon atoms, with a nitro group, or with a halogen;

Signed and Sealed this

Twenty-fourth Day of April 1979

[SEAL]

Attest:

RUTH C. MASON
*Attesting Officer*

DONALD W. BANNER
*Commissioner of Patents and Trademarks*